United States Patent [19]

Peterson et al.

[11] Patent Number: 4,760,030

[45] Date of Patent: Jul. 26, 1988

[54] QUANTITATIVE OPAQUE PARTICLE AGGLUTINATION ASSAY

[75] Inventors: Paulette Peterson, Menlo Park; Martin Becker, Palo Alto, both of Calif.

[73] Assignee: Syntex (U.S.A.) Inc., Palo Alto, Calif.

[21] Appl. No.: 649,253

[22] Filed: Sep. 10, 1984

[51] Int. Cl.$^4$ ............................................. G01N 33/546
[52] U.S. Cl. .................................. 436/509; 436/534; 436/528; 436/805; 436/808; 436/909
[58] Field of Search ............... 436/517, 533, 534, 523, 436/524, 525, 528, 805, 509, 909, 808

[56] References Cited

U.S. PATENT DOCUMENTS

| | | | |
|---|---|---|---|
| 3,689,632 | 9/1972 | Mizushima | 436/805 |
| 4,186,182 | 1/1980 | Gaafar | 436/511 |
| 4,203,724 | 5/1980 | Sawai | 436/519 |
| 4,329,152 | 5/1982 | Lauwerys | 436/534 |
| 4,351,761 | 9/1982 | Gaafar | 424/88 |
| 4,397,959 | 8/1983 | Hechemy | 436/531 |
| 4,401,765 | 8/1983 | Craig | 436/533 |
| 4,418,152 | 11/1983 | Hosaka | 436/531 |
| 4,547,466 | 10/1985 | Turanchik | 436/533 |

FOREIGN PATENT DOCUMENTS 2749956  5/1978  Fed. Rep. of Germany ...... 436/533

OTHER PUBLICATIONS

Crane, Clinical Chemistry, 27(5), p. 697–700 (1981).

*Primary Examiner*—Sidney Marantz
*Assistant Examiner*—Robert Benson
*Attorney, Agent, or Firm*—Theodore J. Leitereg

[57] ABSTRACT

A method is disclosed for determining the presence of a member of a specific binding pair ("sbp member") consisting of ligand and its homologous receptor in a sample suspected of containing the sbp member. The method comprises combining in an assay medium the sample and an opaque particle capable of agglutinating in the presence of the sbp member. The opaque particle has a particle size of from about 0.2 to 5.0 microns. Next, the assay medium is irradiated with light having a wavelength of from about 350 to 2000 nm, and the optical density of the assay medium is measured. A change in optical density indicates the presence of the sbp member in the sample. The method has particular application in the determination of an antibody in a sample, particularly an autoantibody, such as, for example, rheumatoid factor.

18 Claims, No Drawings

QUANTITATIVE OPAQUE PARTICLE AGGLUTINATION ASSAY

BACKGROUND OF THE INVENTION

1. Field of the Invention

There is a continuing need for rapid, accurate, qualitative and quantitative determinations of biologically active substances, e.g., antigens, antibodies, etc., at extremely low concentrations. There is a wide need for determining the presence of drugs in body fluids. In medical diagnoses, it is frequently important to know the presence of various substances which are synthesized naturally by the body or ingested.

Rheumatoid factor represents a heterogeneous population of auto-antibodies that bind to the Fc portion of IgG. It is primarily found as a pentameric IgG but both IgG and IgA forms of the molecule also exist. The detection of rheumatoid factor in serum is used in conjunction with other clinical symptoms for the diagnosis and treatment of rheumatoid arthritis.

The majority of commercial rheumatoid factor (RF) tests are subjective agglutination tests which depend on visual evaluation to determine a semi-quantitative RF titer. These agglutination methods, although simple, are non-instrumented, very subjective and require manual recording of test results. A convenient quantitative, and objective test for RF that can be readily instrumented to avoid transcription errors and permit automation would be useful to the clinician prescribing treatment.

2. Description of the Prior Art

Immunological studies using antigen-coated charcoal and their application to rheumatoid factor are discussed by Gottlieb, et al., *Arthritis and Rheumatism*, 10:199–203 (1967).

Optimization of a sandwich sol particle immunoassay for human chorionic gonadotropin is discussed by Leuvering et al. in the *Journal of Immunological Methods* (1983) 62:175–184. A homogeneous sol particle immunoassay for human chorionic gonadotropin using monoclonal antibodies is discussed by Leuvering et al. in the *Journal of Immunological Methods* (1983) 60:9–23. A homogeneous sol particle immunoassay for total oestrogens in urine and serum samples is disclosed by Leuvering et al. in the *Journal of Immunological Methods* (1983) 62:163–174.

U.S. Pat. Nos. 4,208,185 and 4,118,192 disclose method and apparatus for the measurement of antigens and antibodies. The detection of rheumatoid factor by antibody sensitized microbial particles is described in U.S. Pat. No. 4,189,466.

An agglutination assay for antibodies or antigens by complexion with first reagent particles and agglutinating with second reagent particles in described in Great Britain patent application No. GB 006,686 filed Feb. 26, 1979.

The immunological determination of immune complexes by reacting with immobilized antigen or antibody specific reagents and optionally labeled antibody or antigen specific reagents is disclosed in West German patent application No. DT-836046, filed Aug. 17, 1978.

SUMMARY OF THE INVENTION

A method is provided for determining a member of a specific binding pair ("sbp member") consisting of its ligand and its homologous receptor in a sample suspected of containing the sbp member. The method comprises combining the sample in an assay medium with an opaque particle capable of agglutinating in the presence of the sbp member. The opaque particle has a particle size of from about 0.2 to 5.0 microns. The medium is then irradiated with light having a wavelength of from about 350 to 2000 nm, and the optical density of the assay medium is measured. The presence of the sbp member is indicated by a decrease in optical density. The present method has particular application in the determination of antibodies, particularly auto-antibodies, such as rheumatoid factor.

DESCRIPTION OF THE SPECIFIC EMBODIMENTS

Before proceeding further, a number of terms will be defined.

Analyte—The compound or composition to be measured, which is an sbp member and may be a liguand, which is mono- or polyvalent, that is, having one or a plurality of determinant sites, haptenic and antigenic, a single compound or plurality of compounds which share at least one common epitopic or determinant site; or a receptor.

The ligand analytes are characterized by being mono-epitopic or polyepitopic. The polyepitopic ligand analytes will normally be poly(amino acids), i.e., polypeptides and proteins, polysaccharides, nucleic acids and combinations thereof. Such combinations and assemblages include bacteria, viruses, chromosomes, genes, mitochondria, nucleii, cell membranes, and the like.

For the most part, the polyepitopic ligand analytes employed in the subject invention will have a molecular weight of at least about 5,000 and usually at least about 10,000. In the poly(amino acids) category, the poly(amino acids) of interest will generally be from about 5,000 to 5 million molecular weight, more usually from about 20,000 to about 1 million molecular weight; among the hormones of interest, the molecular weights will usually range from about 2,000 to 60,000.

A number of polyepitopic ligands are described in U.S. Pat. No. 4,275,149, bridging columns 12–17, which disclosure is incorporated herein by reference.

The monoepitopic ligand analytes will generally be from about 100 to 2,000 molecular weight, more usually from about 125 to 1,000 molecular weight.

Monoepitopic analytes are described in U.S. Pat. No. 4,275,149, bridging columns 17 and 18, which disclosure is incorporated herein by reference. Also included in the aforementioned patent is a description of the ligand analog, bridging columns 18 and 19, which disclosure is also incorporated herein by reference.

Sbpt member—A member of a specific binding pair, consisting of two different molecules, where one of the molecules has an area on the surface or in a cavity which specifically binds to a particular spatial and polar organization of the other molecule. The members of the specific binding pair are referred to as ligand and receptor (antiligand) and are also referred to as homologous.

(a) Ligand-Any organic compound for which a receptor naturally exists or can be prepared.

(b) Receptor (antiligand)—Any macromolecular compound or composition capable of recognizing (having an enhanced binding affinity to) a particular spatial and polar organization of a molecule, i.e., epitopic or determinant site. Illustrative receptors include naturally occurring receptors, e.g., thyroxine binding globulin, antibodies, enzymes, Fab fragments, lectins, and the like. The term antibody is employed in this case as illustrative of, and to more generally denote, receptor. Naturally occurring or synthetic.

Opaque particle—particle which is naturally occurring or synthetic, insoluble, water suspendable, chemically or physically activatable to permit attachment of an sbp member, absorbing light at the wave length of the assay sufficient to reduce transmittance of an assay medium by at least 40%, such as carbon, metal sols, dye aggregates, etc, preferably carbon, usually absorbing light of a wavelength between about 350 to 2000 nm.

Ligand Analog—A modified ligand which can compete with the analogous ligand for a receptor, the modification providing means to join a ligand analog to another molecule. The ligand analog will normally differ from the ligand by more than replacement of a hydrogen with a bond which links the ligand analog to a hub or label.

Poly(ligand-analog)—A plurality of ligands or ligand analogs joined together covalently, normally to a hub nucleus. The hub nucleus is a polyfunctional material, normally polymeric, usually having a plurality of functional groups, e.g., hydroxy, amino, mercapto, ethylenic, etc., as sites for linking. The hub nucleus may be water soluble or insoluble, preferably water soluble, and will normally be at least about 35,000 molecular weight and may be 10 million or more molecular weight, but usually under 600,000, more usually under 300,000. Illustrative hub nucleii include polysaccharides, polypeptides, including proteins, nucleic acids, ion exchange resins, and the like.

The present invention provides a method for determining an sbp member in a sample suspected of containing the sbp member. The method is applicable to a determination of a wide variety of analytes in a sample including both antigens haptins and antibodies. Exemplary of such analytes are those described in U.S. Pat. No. 4,160,645 columns 6 to 13, which description is incorporated herein by reference.

As mentioned above, the present method has particular applicability in the determination of antibodies, directed against both self and non-self antigens, including antibodies in a sample suspected of containing such antibodies. The method may be used to detect a wide variety of antibodies that are currently assayed by agglutination, such as rheumatoid factor, anti-rubella, anti-toxoplasmosis heterophile antibody, and anti-cardiolipin and the like.

The present method is particularly applicable in the determination of auto-antibodies in a sample. Such auto-antibodies include, but are not limited to, rheumatoid factor, anti-ds.DNA, anti-thyroglobulin, anti-insulin, anti-islet cell receptors, and so forth The present method may also be employed in the detection of fragments of antibodies such as Fab, Fv, Fc, and the like.

The sample suspected of containing the analyte is combined in an assay medium with an opaque particle capable of agglutinating in the presence of the sbp member. The opaque particle has a particle size of from about 0.2 to 5.0 microns, preferably from about 0.2 to 1.0 microns, more preferably from about 0.3 to 0.4 microns and is preferably substantially non-associating.

The subject method is carried out in an assay medium, generally an aqueous assay medium, at a pH of from about 6–10, preferably from about 8.0 to 9.8, more preferably from about 9.0–9.5. The assay medium is normally buffered. The buffers which may be used to achieve the desired pH and maintain the pH during the determination are, for example, borate, phosphate, carbonate, Tris, barbital, and the like. The particular buffer employed in the present method is not critical, but in individual assays, one buffer may be preferred over the other.

The assay medium may also contain a polar organic solvent having from 1–6 carbon atoms and from 1–3 heteroatoms selected from the group consisting of oxygen, nitrogen, and sulphur. Such solvents include alcohols, ethers, and the like. Usually these solvents will be present in less than about 40 weight precent (wt %), more usually in less than about 20 wt %.

The sample is combined in the assay medium with an opaque particle capable of agglutinating in the presence of the sbp member. The capability of agglutinating in the presence of the sbp member may be naturally possessed by the opaque particle because of the presence of an sbp member on its surface or the opaque particle will be treated to render it capable of agglutinating in the presence of the sbp member. In the latter situation, the opaque particle will be conjugated to a specifc binding partner of the sbp member. The conjugation of the opaque particle with the specific binding partner of the sbp member may be carried out in a conventional manner by adsorption through incubation of the particles with the sbp member or by covalent coupling as, for example, by linking carboxyl groups naturally present on the surface of carbon with amino groups of a protein by means of carbodiimide coupling.

The conjugation or adsorption may be direct or indirect. By direct conjugation is intended covalent bonding of the specific sbp member to the particle according to standard techniques. Alternatively, an sbp member can be indirectly bound by non-covalent binding to a complementary sbp member bound to the particle. Where the sbp member is multivalent, an impure preparation of a complementary member may be covalently bonded to the particle. Noncovalent binding of the unpurified sbp member then gives a particle labeled with the sbp member. Adsorption of the sbp member to the particle may be accomplished according to conventional methods.

The ratio of the number of sbp members to the surface area of the particle will vary widely, depending upon the nature of the particle, the available binding sites, and the like. There will be on the average at least about one sbp member per particle and generally at least about one per 100,000 $Å^2$ surface area, more usually at least about one per 10,000 $Å^2$ surface area.

The opaque particle is preferably substantially non-self-associating which means that the particle size remains in the range of about from 0.2–5.0 microns, preferably 0.2–1.0 microns, more preferably, 0.3–0.4 microns. In a preferred embodiment of the present invention, the assay medium further contains an amino acid having from 2 to 10 carbon atoms and 3 to 6 heteroatoms selected from the group consisting of oxygen, nitrogen, and sulphur, such as, for example, glycine, serine, cysteine, aspartic acid, asparagine, etc. The amino acid is included in the assay medium in an effective amount, i.e., an amount sufficient to substantially reduce self-agglutination of the opaque particle. For this purpose, the assay medium usually will contain the amino acid in an amount of from about 0.005–0.10 molar, preferably 0.01 to 0.02 molar.

To further reduce self-agglutination of the opaque particle, the particle may be coated with a protein, such as a plasma protein, for example, bovine serum albumin, rabbit serum albumin, gelatin, and the like, in an effective amount, i.e., an amount sufficient to substantially reduce self-agglutination of the particle. Thus, the particle may be coated with from about 0 to 50 wt %, preferably from about 10 to 30 wt %, of the protein. The particle may be coated by adsorption, covalent binding, or the like.

The combined sample and opaque particle in the assay medium may be irradiated immediately or may be incubated, i.e., held, for a time and under conditions for agglutinating the particles. In general, the combination may be held for a period of from 30 seconds to about 60 minutes and, where a holding period is employed, preferably a period of from about 10 to 30 minutes.

Moderate temperatures are normally employed for carrying out the assay and usually a constant temperature is employed. The temperature for the assay will generally be in the range of from about 10°–50° C., more usually from about 20°–40° C. Preferably, the assay medium is agitated during the holding period. Such agitation may be accomplished by conventional means such as orbital shaking, stirring, sonication, etc.

The concentration of analyte which may be assayed will generally vary from about $10^{-4}$ to $10^{-20}$ M, more usually from about $10^{-6}$ to $10^{-16}$ M. Considerations such as whether the assay is qualitative, semi-quantitative or quantitative, the particular detection technique and the concentration of the analyte of interset will normally determine the concentration of the other reagents.

While the concentrations of the various reagents in the assay medium will generally be determined by the concentration range of interest of the analyte, the final concentration of each of the reagents will normally be determined empirically to optimize the sensitivity of the assay over the range of interest. The total binding sites of the members of the specific binding pair which are reciprocal to the analyte will be not less than about 0.1 times the minimum concentration of interest based on binding sites of analyte and usually not more than about 1,000 times the maximum concentration of interest based on analyte binding sites, usually about 0.1 to 100 times, more usually about 0.3–10 times the maximum concentration of interest. By concentration is intended the available concentration, that is, the concentration at saturation, and not necessarily the actual concentration where members of the specific binding pair may not be equally available for binding.

Depending upon the manner in which the specific binding pair members are employed, the amount of the various conjugates can be varied quite widely. By employing various concentrations of the various reagents with analyte at concentrations in the range of interest, one would obtain ratios which would optimize the assay response.

The order of addition of the various reagents may vary widely depending upon the nature of the opaque particle conjugate, the nature of the analyte, and the relative concentrations of the analyte and reagents.

As mentioned above, the analyte (ligand) may be mono- or polyepitopic. In most situations this difference need not affect the manner in which the assay is performed. Where the analyte is a ligand, the sbp member in the opaque particle conjugate may be either ligand or receptor, being the same or different, normally being a receptor. However, where the analyte and the sbp member in the particle conjugate are the same, a homologous sbp member must be provided in polyvalent form as an additional reagent. Where the homologous sbp member is a receptor, it is usually either an antibody or a polyvalent receptor. Where the homologous sbp member is a ligand, it is usually a polyhapten or poly(ligand analog). That is, a sandwich technique is employed where the homologous sbp member as an additional reagent binds to the particle conjugate and provides binding sites for agglutination to occur in the presence of the analyte.

The assay medium is next irradiated with light having a wavelength of from about 350 to 2000 nm, preferably from about 500 to 800 nm. The light source may be a conventional tungsten lamp, a source of coherent light, e.g., a laser, a Xenon source, etc. In the case of non-coherent light, the wavelength light emitted from a light source is selected by a filter or prism so as to apply a light beam of a specific wavelength range. Filters or prisms employed are standard. The light is converged approximately through a slit or lens before it is applied to the sample.

During the irradiation step, the assay medium is conveniently held in a container compatible to the apparatus used in carrying out the irradiation, such as, a cuvette or flow cell. The container may be composed of transparent glass or synthetic resin, for example, acrylic resins, and may generally have an oroid or rectangular cross-section. The cell thickness, that is, the distance between windows, respectively, on the side from which the light is applied and on the opposite side, may be in the range of 0.5 to 20 millimeters, preferably 1–10 millimters. The transmissive windows may advantageously possess at least 30% transmission, preferably 80% or higher transmission for light in the wavelengths described about.

During irradiation of the assay medium, the optical density of the assay medium is measured The optical density may be measured in a conventional manner using standard equipment such as, for example, a spectrophotometer, colorimeter, or the like. A change in optical density of the assay medium indicates the presence of the analyte of interest. Generally, a decrease in the optical density of the assay medium indicates the presence of the analyte of interest. However, where a poly(ligand analog) is employed an increase in optical density of the assay medium indicates the presence of the analyte of interest.

Calibrators can be prepared which have known amounts of the analyte. The observed optical density for the calibrators may then be plotted so as to relate concentration to optical density. Once a standard curve has been established, an optical density of a sample suspected of containing the analyte assayed in accordance with the present invention may be directly related to the concentration of the analyte.

Various ancillary materials may be employed in the subject assays. Particularly, bulking agents, buffers, stabilizers, biocides, detergents, specialized additives and the like may be added to the assay medium. The ancillary materials generally will be present in relatively small amounts, usually less than about 1 M, more usually less than about 0.5 M. Buffers will normally be present to provide an assay medium at a pH in the range described above. Particular ancillary materials include non-ionic detergents, sodium azide, serum albumin, gamma globulin, Tris, trace metals, salts, sodium chloride, etc. The ionic strength of the assay medium should usually be, from about 0.01 to 1.0, preferably 0.01 to 0.05. Bulking agents, such as destran, sucrose, etc., may be added to decrease reagent settling in the assay medium. Preferably, these bulking agents are added to a concentration in the assay medium of from about 0 to 5%.

As a matter of convenience, the reagent can be provided in kits or packaged combinations, where the reagents are in predetermined ratios, so as to substantially optimize the sensitivity of the assay in the range of interest. Included with the kits will normally be the ancillary materials, and any other reagent necessary for performing the assay.

The method of the present invention is a convenient, quantitative, and nonsubjective method for detecting sbp members, such as rheumatoid factor, in a sample suspected of containing the sbp member. The method offers many advantages, one of the most important of which is the elimination of operator bias that is present in the majority of agglutination assays. A single, easily prepared reagent is employed, and the assay protocol is easily automated. The results can be monitored on a variety of instrumentation, such as a spectrophotometer, or the like.

EXAMPLES

The following examples are offered by way of illustration and not by way of limitation. All percents in parts not otherwise indicated are by weight, except for mixtures of liquids which are by volume. All temperatures not otherwise indicated are centigrade.

The following materials were employed:
Chemicals
Carbon black: Sterling RV5373, Cabot Corp.
Ethylene Diamine Tetraacetate (EDTA): M.W. 336.2, lot 49C-0507, Sigma
Glycine: M.W. 75.07, lot E9B, Eastman
$NaN_3$: M.W. 65.01, lot B9A, Eastman Kodak
NaCl: 58.44, analytical grade, Mallinckrodt Corp.
$Na_2HPO_4$: M.W. 141.96, analytical grade, Mallinckrodt Corp.
Biochemicals
Bovine Serum Albumin (BSA): Lot 61, Miles Laboratories
Human Immune Globulin (HuIgG): Affinity purified, lot 42, Miles Laboratories
ICS-RF: Rheumatoid factor (RF) reagent test kit, Beckman Industries
Rheumanosticon: RF latex agglutination test, Organon Sera were titered with Rheumanosticon latex agglutination test, aliquoted, and stored frozen on day received, unless otherwise noted.

Serum standards were prepared by serially diluting a high titer RF sample into normal serum.
Buffers
Glycine: 0.17 M, 0.1 M NaCl, pH 9.2, 0.1 M, 0.15 M Nacl, pH 8.6, 0.02% $NaN_3$, 0.05 M, 0.15 M Nacl, pH 8.6, 0.02% $NaN_3$, 0.01 M, 0.15 M Nacl, pH's 7.5, 8.5, 9.5, 0.02% $NaN_3$,
PBS: 0.01 M, 0.25 M Nacl, pH 7.4, 1% BSA, 0.02% $NaN_3$,
Phosphate: 0.1 M, pH 7.4, 0.1% BSA.

EXAMPLE 1

Preparation of IgG Coated Carbon

The Sterling Carbon used to prepare the IgG-carbon conjugate was first boiled in EDTA and HCl to remove any residual metals and organics.

Sterling Carbon (100 g) was boiled with stirring in 1.5 l of glass distilled $H_2O$ containing 1 mM EDTA for 10 min. The hot solution was filtered through a large, porcelain Buchner funnel. The cake of carbon was placed in 1 l of boiling 1N HCl for 10 min. Again, the hot carbon slurry was filtered through a Buchner funnel. The cleaned carbon was then washed in boiling water and filtered. The washing and filtering were repeated until the effluent had a pH of 5. The cleaned carbon was dried in a vacuum oven at 100° C. for 2 hours. After 2 hours, the carbon was finely ground with mortar and pestle and dried to constant weight in the vacuum oven.

The cleaned carbon (380 mg) from above was suspended in 9.5 ml of 0.17 M glycine containing 0.1 M NaCl at pH 9.2. The carbon and glycine were probe sonicated in a 30 ml glass centrifuge tube for 2 to 3 min. During the sonication, the suspension was magnetically stirred on ice. While sonicating and stirring, 9.55 ml of 0.17 M glycine with 0.1 M NaCl at pH 9.2 containing 190 mg of dialyzed HuIgG was added and the mixture was sonicated on ice for an additional minute. The particle size was measured as 0.3 $\mu$. The IgG and carbon were rotated overnight at room temperature in the glass centrifuge tube. After incubation, the IgG coated carbon was resonicated for 1 min. and palleted at 10°–15° K. for 5–10 min. The supernatent was saved to determine percent binding, and the carbon was washed three times with glycine and sonication. Approximately 40% of the HuIgG bound to the carbon.

The IgG coated carbon was sonicated in approximately 20 ml of 0.17 M glycine containing 0.1% BSA and was incubated with rotation for 2–3 hours at room temperature. The excess BSA was washed away three times with 20 ml washes of 0.17 M glycine and sonication.

The conjugate was stored in 0.01 M glycine containing 0.15 M NaCl and 0.01% $NaN_3$ at pH 9.5. The storage dilution was such that 12.5 $\mu$l of the stock HuIgG coated carbon, when diluted in 1.5 ml of buffer, gave an $OD_{550}$ of 0.5. Tthe conjugate was stored at 4° C. in stoppered glass tubes.

EXAMPLE 2

Assayed for Rheumatoid Factor

A portion of the carbon conjugate from Example 1 was diluted 1:2 in a buffer of 0.01 M glycine at pH 9.5 containing 150 mM NaCl. The diluted carbon (200 $\mu$l), 10 $\mu$l of sample and 90 $\mu$l of buffer were incubated at room temperature in 13×100 mm glass test tubes on a mini-orbital shaker at setting 4.5. After 30 min. of shaking, the volumes were diluted to 3 ml with the buffered glycine. The 2.7 ml of glycine buffer sufficiently suspended the agglutinated carbon and no vortexing was required. The samples were read at 700 nm on a Gilford Stasar ® spectrophotometer.

Thirty-one fresh-frozen samples and a set of serum standards were assayed by latex agglutination test, Beckman's KS-RF method, and the method according to the present invention. All 31 samples were detected and ranked by present method and the Organon latex assays. These tests correlated well with an R square value of 0.996 and a slope of 0.98.

Only 13 of the 31 samples were detected by the Beckman ICS-RF test. Seventeen of the samples registered as out of range low on the ICS-RF.

As is evident from the above results, the assay of the present invention was more sensitive than the Beckman ICS-RF assay, detected a wider range of concentrations than the Beckman ICS-RF assay, and required less technician time than either the Organon latex assay or the Beckman ICS-RF. In addition, the present method is not subjective as is Organon latex test.

Although the foregoing invention has been described in some detail by way of illustration and example for purposes of clarity and understanding, it will be obvious that certain changes or modifications may be practiced within the scope of the appended claims.

What is claimed is:

1. A method for determining a member of a specific binding pair ("sbp member") consisting of ligand and its homologous receptor in a sample suspected of containing said sbp member, which comprises
    (a) combining in an assay medium the sample and an opaque particle which is a carbon particle conjugated to an sbp member complementary to said sbp member and capable of agglutinating in the presence of said sbp member, said opaque particle having a particle size of from about 0.2 to 5.0 microns and being present in an amount sufficient to reduce transmittance of said assay medium by at least 40% at a wavelength of 350 to 800 nanometers, the pH of said medium being about 8.0–9.8, said medium containing an amino acid having from 2 to 10 carbon atoms in an amount sufficient to reduce self-agglutination of said opaque particles, and
    (b) measuring the optical density of the assay medium at said wave length wherein a decrease in optical density from that of the assay medium prior to agglutination indicates the presence of said sbp member in said sample.

2. The method of claim 1 wherein the sbp member of said sample is an antibody.

3. The method of claim 1 wherein the sbp member of said sample is an autoantibody.

4. The method of claim 1 wherein the sbp member of said sample is rheumatoid factor.

5. The method of claim 1 wherein the opaque particle is conjugated to a specific binding partner of said sbp member by adsorption.

6. The method of claim 2 wherein the antibody is rheumatoid factor and the opaque particle is conjugated to immunoglobulin G.

7. The method of claim 1 wherein the particle size is from about 0.3–0.4 microns.

8. The method of claim 1 wherein said amino acid is glycine.

9. The method of claim 8 wherein said assay medium contains glycine in an amount of from about 0.005–0.02 molar.

10. The method of claim 1 wherein said opaque particle is coated with a protein in an amount sufficient to subtantially reduce self-agglutination of said particle.

11. The method of claim 10 wherein said protein is a plasma protein.

12. The method of claim 10 wherein said protein is bovine serum albumin in an amount of up to 50% by weight.

13. The method of claim 1 wherein the assay medium from Step (a) is incubated prior to measuring the optical density in Step b.

14. A method for determining the presence of an antibody in a sample suspected of containing said antibody, which comprises
    (a) combining, in an assay medium, the sample and a conjugate of a carbon particle and a specific binding partner for said antibody, said conjugate being subtantially non-self-agglutinating and having a particle size of from about 0.2 to 1.0 microns and being present in an amount sufficient to reduce transmittance of said assay medium by at least 40% at a wavelength of 400 to 800 nanometers, the pH of said medium being about 8.0-9.8, said medium containing an amino acid having from 2 to 10 carbon atoms in an amount sufficient to reduce self-agglutination of said opaque particle, and
    (b) measuring the optical density of the assay medium at said wavelength and comparing the optical density to that of a calibrator assay medium containing a known amount of antibody and subjected to steps (a) and (b) above wherein a decrease in optical density indicates the presence of antibody in said sample.

15. An assay method for determining the presence of rheumatoid factor in a sample of a biological fluid which method comprises
    (a) combining in an aqueous assay medium the sample and a conjugate of a carbon particle and immunoglobulin G, said conjugate being coated with albumin and having a particle size of from about 0.3 to 0.4 microns and being present in an amount sufficient to reduce transmittance of said assay medium by at least 40% at a wavelength of 600 to 800 nanometers, said medium being about 0.005 to 0.02 molar in glycine and having a pH of about 9.0 to 9.5,
    (b) incubating the assay medium with agitation, and
    (c) measuring the optical density of the assay medium at said wavelength and comparing the optical density to that of a calibrator assay medium containing a known amount of rheumatoid factor and subjected to steps (a), (b) and (c) above wherein a decrease in optical density indicates the presence of rheumatoid factor in said sample.

16. A composition comprising a conjugate of a carbon particle and immunoglobulin G in an aqueous buffered medium at pH 9.0 to 9.5, said medium being 0.005 to 0.02 molar in glycine, said conjugate having a particle size of from about 0.2 to 1.0 microns.

17. The composition of claim 16 wherein said conjugate is coated with albumin.

18. A kit for performing an assay for rheumatoid factor, which comprises
    the composition of claim 16 in an effective amount for the determination of rheumatoid factor.

* * * * *